United States Patent
Mahy et al.

(10) Patent No.: US 6,387,396 B2
(45) Date of Patent: *May 14, 2002

(54) COMPOSITIONS CONTAINING AT LEAST ONE NUCLEIC ACID

(75) Inventors: Patrick Mahy, Talence; Didier Roux, Merignac; René Laversanne; Joëlle Amedee, both of Pessac; OLivier Freund, Bordeaux, all of (FR)

(73) Assignee: Capsulis, Pessac (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,475

(22) PCT Filed: Jul. 15, 1997

(86) PCT No.: PCT/FR97/01304

§ 371 Date: Jan. 6, 1999

§ 102(e) Date: Jan. 6, 1999

(87) PCT Pub. No.: WO98/02144

PCT Pub. Date: Jan. 22, 1998

(30) Foreign Application Priority Data

Jul. 16, 1996 (FR) .............................................. 96 08844

(51) Int. Cl.$^7$ .............................................. A61K 9/127
(52) U.S. Cl. .................... 424/450; 424/1.211; 424/417; 424/420; 435/458
(58) Field of Search .............................. 424/450, 1.211, 424/417, 420; 435/320.1, 458; 514/44; 264/4.1

(56) References Cited

U.S. PATENT DOCUMENTS

| | | | |
|---|---|---|---|
| 4,394,448 A | * 7/1983 | Szoka et al. ................ 435/458 |
| 5,169,637 A | * 12/1992 | Lenk et al. ................ 424/450 |
| 5,234,634 A | * 8/1993 | Janoff et al. ................ 264/4.1 |
| 5,593,972 A | * 1/1997 | Weiner et al. ................ 514/44 |
| 5,627,159 A | * 5/1997 | Shih et al. ................ 514/44 |
| 5,672,358 A | * 9/1997 | Tabibi et al. ................ 424/450 |
| 5,723,147 A | * 3/1998 | Kim et al. ................ 424/450 |
| 5,827,531 A | * 10/1998 | Morrison et al. ........... 424/450 |
| 5,916,588 A | * 6/1999 | Popescu et al. ............. 424/450 |
| 6,001,644 A | * 12/1999 | Debs et al. ................ 435/320.1 |

FOREIGN PATENT DOCUMENTS

| | | |
|---|---|---|
| DE | 4005152 | 8/1991 |
| EP | 0424688 | 5/1991 |
| WO | 95/16437 | 6/1995 |
| WO | WO 95/18601 | * 7/1995 |
| WO | 97/04748 | 2/1997 |
| WO | 97/10851 | 3/1997 |

OTHER PUBLICATIONS

Juliano et al (Antisense Res Dev 1992 Summer;2(2):165–76, absract only.*
Verma et al. Nature 389: 239–242, especially p. 239, Sep. 1997.*
Anderson et al. Nature 392: 25–30, especially pp. 25 and 30, Apr. 1997.*
Eck and Wilson. In Goodman and Gilmans the Pharmacological basis of Therapeutics. McGraw–Hill publishers. pp. 77–101, especially 77–82, in particular p. 81 column 2 to p. 82 col. 2, 1995.*
Boros et al.; High–copy–number derivatives of the plasmid cloning vector pBR322, 1984, Gene 30: 257–260.*

* cited by examiner

Primary Examiner—James Ketter
Assistant Examiner—Richard Schnizer
(74) Attorney, Agent, or Firm—Dennison, Scheiner 7 Schultz

(57) ABSTRACT

A composition containing a plurality of multicellular vesicles and at least one nucleic acid, at least one part of which is found included inside the multilamellar vesicles. Each of the vesicles is formed of a succession of lamellar bi-layers extending from each vesicle center to its periphery and including at least one surfactant agent. The bi-layers are concentric and are separated by a liquid medium. Such compositions can be used in pharmaceutics, particularly gene therapy, and in in vitro and in vivo transfection.

24 Claims, 1 Drawing Sheet

COMPOSITIONS CONTAINING AT LEAST ONE NUCLEIC ACID

BACKGROUND OF THE INVENTION

The invention relates to new compositions containing at least one nucleic acid and their applications in the biomedical field, particularly in gene therapy.

Up to the end of the Eighties, the use of liposomes in view of biomedical applications and, more specifically, in gene therapy did not seem very promising. The results of transfection (translation and expression of a gene of prokaryotic or eukaryotic cells by eukaryotic cells), essentially transient, were relatively mediocre. The recourse to external virus envelopes has very significantly added to the results of gene transfers in a multitude of cell lines in vitro. On the contrary, it is certain that their use in human therapy and animal therapy gives rise to problems given the possible iatrogenic dangers that they represent. Towards the end of the last decade, it appeared that the use of cationic surfactants very clearly improved the results of transfection. Since then, despite certain problems linked to the use of cationic vectors, many formulations have been proposed some of which are patented and marketed.

In general, three sorts of non-viral vectors are used:
cationic polymers,
biochemical vectors constituted of a cationic protein combined with a cell receptor,
cationic lipids associated or non-associated to liposomes.
All these vectors contain cationic molecules.

The use of such vectors is notably found described in the following publications:

J. P. Behr et al. Proc. Nat. Ac. Scienc. 86, 6982, 1989
M. Cotten and Wagner Curr. Opin. Cell Biol. 4, 705, 1993
J. Haensler and F. C. Szoka Bioconjug. Chem. 4, 372, 1993
C. P. Hodgson Bio Technology 13, 222, 1995
F. D. Ledley Hum. Gene Ther. 6, 1129, 1995
J. S. Remy et al. Proc. Nat. Ac. Scienc. 92, 1744, 1995
V. S. Trubettskoy et al. Biochem. Biophys, Acta 1131, 311, 1992

Two essential problems arise from the use of cationic vectors
1—these surfactants are generally cytotoxic and even if certain specific molecules have been developed in order to reduce the toxicity thereof, the problem is not entirely solved,
2—their application cannot be envisaged in vivo since these vectors, due to their charge, interact very strongly with proteins, for example, with those present in the serum, as well as with the cell walls. They therefore stick rapidly onto the cells neighbouring the site of injection, reducing the systemic diffusion thereof.

This is the reason why they find their preferential use in vitro for cells in culture, in the transfer of genes.

It is well known that liposomes are colloidal structures which comprise an aqueous core separated from the external medium by one or more bi-layers of phospholipid molecules. Their application in cosmetics and in pharmacology has been the subject of a large number of patents which describe many uses of these vectors since their discovery in the 1960's.

From the point of view of applications, liposomes composed of one sole bi-layer, liposomes composed of several bi-layers often designated by the abbreviation MLV which corresponds to <<Multi-layered Vesicles>>, have been very rapidly distinguished. The multi-layered vesicles have a size which is badly controlled and is generally far greater than a micrometer. Amongst the uni-lamellar vesicles, small vesicles, often designated as the abbreviation SUV corresponding to <<Small uni-lamellar vesicles>> the size of which does not exceed 100 to 300 nm, have been distinguished from large vesicles often designated by the abbreviation LUV corresponding to <<Large uni-lamellar vesicles>> which can attain several tens of micrometers in size.

From the fact of their significant size, the multilamellar vesicles (MLVs) are only of little use in medical applications. In fact, risks of embolism that the introduction of particles of size of greater than a micrometer into the blood circulation brings about render their use impossible by intra-venous injection. Moreover, too great a size hinders the vesicles from passing through the tissue barriers, and this enables finding them in -the blood when they are injected intramuscularly or sub-cutaneously. Finally, really efficient processes do not exist for producing MLVs in a perfectly controlled way. The major part of the applications have been developed with SUVs which fulfil the criteria of safety and control necessary for a biomedical use.

The encapsulation of nucleic acids in vesicles based on surfactants, generally lipidic surfactants, has also been described in the literature. All the vesicles described to date have in common the fact of having several layers of surfactants surrounding a liquid core. Such vesicles are described, in particular, in the patents U.S. Pat. Nos. 4,394,448 and WO-95/16437.

One of the practical problems of the use of liposomes for the vectorisation of medicaments or their use in gene therapy is the low yield due to the fact that the percentage of the starting aqueous solution effectively encapsulated rarely exceeds 30%. Moreover, the method generally followed calls for steps of evaporation of organic solvents which intervene in the method of preparation. Finally, the experimental results have revealed to be very deceiving.

In fact, the methods commonly accepted for the incorporation of lipidic vesicles, or cationic complexes which contain DNA, in the cells, pass via a mechanism of endocytosis. In the cytoplasm, the object undergoing penetration is included in an endosome which contains enzymes, in particular DNAses which are capable of destroying any intruding genetic material. The liposomes, due to their low number of lipidic membranes which surround the aqueous core, do not provide sufficient protection for resisting the destructive action of the endosomal nucleases and proteases. From this, even if they are efficient in penetrating the cytoplasm of the cell, the liposomes enable the DNA to reach the nucleus with only a low yield.

It is therefore crucial to develop synthetic vectors which are compatible with an in vivo use and this all the more so since there does not exist at present an efficient vector for molecules which can be applied in human and/or animal gene therapy. Alone, the viral envelopes show an efficiency in transfection which is compatible with a human or animal application.

The vesicles of the liposome type or paucilamellar vesicles have in common to be constituted of one or more lamellar layers surrounding an aqueous core. Apart from this type of vesicles, multi-lamellar vesicles are also known which are structurally different from the preceding ones by the fact that they have a structure known as an <<onion>> structure and are constituted, from their centre through to their periphery, of a succession of lamellar layers which are separated by a liquid medium. These vesicles may be obtained by a method which comprises the preparation of a liquid crystal lamellar phase and its transformation by the application of a shearing. Such a method is described in particular in the by patent WO 93/19735 originating from French patent FR-2 689 418 or WO 95/18601 introduced herein by reference.

According to French patent FR-2 689 418, this transformation may be made during a homogenous shearing step of the liquid crystal phase, and this leads to vesicles which are known as microcapsules of controlled size. However, in adjusting the formulation of the liquid crystal lamellar phase, in particular in adjusting the nature of the surfactants entering in its composition, the transformation of this liquid crystal phase into vesicles can be obtained by a simple mechanical manipulation, in particular during the mixing of the constituents.

SUMMARY OF THE INVENTION

The research conducted by the inventors have lead them to discover that the use of the technologies described above allowed developing new multi-lamellar vectors of small size, which are non-cationic, and which enable encapsulating, protecting, and delivering DNA into cells; and all this with a high encapsulation efficiency as well as with a great ease of preparation.

Another advantage is that all the molecules which enter into the preparation of the compositions of the invention are commercially available.

Another advantage of the method enabling the preparation of the compositions of the invention is that it enables using a large variety of surfactants.

According to another advantage, the invention provides a vehicle which enables, very probably due to the fact of its specific structure, protecting the nucleic acid from external attack, in particular from enzymatic attack. This point is illustrated in Example 1. This constitutes a clear advantage with respect to liposomes and to classical paucilamellar vesicles which are merely not very efficient in transfection, probably because they are not capable of protecting the DNA from the action of DNAses present in the endosome in particular. The power of the technology of the invention is partially due to this protection of the nucleic acids against nucleases. It may be supposed, without it constituting a certain explanation in the actual state of knowledge of the inventors, that the first layers of the multi-lamellar vesicle are effectively destroyed by enzymatic action in the endosome, but sufficient encapsulated DNA remains during the rupture of the endosome, so as to have a release of this DNA into the cytoplasm, which is thus capable of reaching the nucleus. Moreover, the high concentration of surfactants in the vesicles of the invention could enhance, during the erosion of the first layers, the destabilisation of the endosome by the action of the released surfactants upon the walls of the endosome.

According to another of its advantages, the invention enables, if need be, incorporating products of cationic character into the compositions, which products are already known for their importance in transfection, the other ingredients of the composition of the invention enabling masking the cationic character of this molecule, thus enabling using it for in vivo applications. Thus, the invention therefore further provides a means of increasing the efficiency or lowering the toxicity of a cationic molecule known for its use in transfection. In fact, most of the cationic compounds used are cytotoxic, and this cytotoxicity can be decreased by encapsulating these molecules, and this constitutes a further advantage of the invention.

Other advantages appear from the description and the Examples which follow, wherefrom it may be seen that this type of vector enables significantly overcoming all the problems set forth above and enables offering, for the first time, a vehicle, in the form of vesicles based on surfactants, which may be used in vivo.

The invention relates, according to one of its essential characteristics, to a composition which contains at least one nucleic acid at least one part of which is found included inside multilamellar vesicles, characterised in that said vesicles are constituted of bi-layers comprising at least one surfactant agent, said bi-layers being concentric and giving an onion structure to said vesicles.

<<Onion>> structure is understood as meaning, as set forth above, a multi-lamellar structure in which the vesicles of substantially spherical shape are constituted of a succession of concentric bi-layers, this being from the centre to the periphery of the vesicles, from which the name of onion structure is used, by analogy, for qualifying such structures.

Such structures are advantageously obtained by incorporating at least one nucleic acid in a liquid crystal lamellar phase which comprises at least one surfactant agent, and then transforming this lamellar liquid crystal phase into a dense phase of small-sized multi-lamellar vesicles.

Thus, according to another essential characteristic of the invention, the invention relates to a method of preparation of a composition which contains at least one nucleic acid as defined above, according to which method, a lamellar liquid crystal phase is prepared which incorporates said nucleic acid, and the rearrangement of said liquid crystal phase into multi-lamellar vesicles is caused by the application of a shearing.

This shearing may be a homogenous shearing, and this has the advantage of leading to vesicles of perfectly homogenous size. However, a simple mechanical stirring may prove to be sufficient to lead to the formation of the multi-lamellar vesicles of the invention.

According to yet another characteristic, the invention relates to the products which are obtainable by this method.

According to French patent FR-2 689 418, this transformation may be made during a homogenous step of shearing of the liquid crystal phase, and this leads to vesicles or microcapsules of controlled size. However, in adjusting the formulation of the liquid crystal lamellar phase, in particular in adjusting the nature of the surfactants entering in its composition, the transformation of this liquid crystal phase into vesicles can be obtained by simple mechanical manipulation, in particular during the mixing of the constituents.

The formulation advantageously includes a mixture of surfactant molecules. At least two different surfactants are generally used which have different hydrophilic lipophilic balances, and this enables continuously regulating the properties of the bi-layers, and thus enables controlling the appearance of instability which governs the formation of the multi-lamellar vesicles.

According to an advantageous variant, the vesicles which constitute the compositions of the present invention are of dimensions which are less than 1 $\mu$m, preferably between 0.1 and 1 $\mu$m.

According to another advantageous variant of the invention, the surfactants which constitute the bi-layers of the vesicles are non-cationic surfactants, and this, as has been seen previously, has a great advantage over the compositions of the prior art which make use of cationic molecules.

According to an advantageous variant, the membranes of the vesicles contained in the compositions of the invention advantageously contain at least one surfactant agent selected from the group consisting of:

hydrogenated or non-hydrogenated phospholipids,
saturated or mono- or polyunsaturated, linear or branched $C_6$ to $C_{18}$ fatty acids, in the form of an acid or an alkali metal salt, an alkaline earth metal salt, or an amine salt,
ethoxylated or non-ethoxylated esters of the same fatty acids and
  of sucrose,
  of sorbitan
  of mannitol,
  of glycerol or of polyglycerol,
  of glycol,
mono-, di- or triglycerides or mixtures of glycerides of the same fatty acids,
saturated or mono- or polyunsaturated, linear or branched, ethoxylated or non-ethoxylated $C_6$ to $C_{18}$ fatty alcohols,
ethoxylated or non-ethoxylated ethers of the same fatty alcohols and
  of sucrose,
  of sorbitan,
  of mannitol,
  of glycerol or of polyglycerol,
  of glycol,
hydrogenated or non hydrogenated polyethoxylated vegetable oils,
block polymers of polyoxyethylene and polyoxypropylene (poloxamers),
polyethylene glycol hydroxystearate,
sterol-skeleton alcohols such as cholesterol, sistosterol.

According to an advantageous variant, the surfactants entering in the composition of the bi-layers of the vesicles are constituted of non-cationic surfactants.

The surfactants selected, in particular the surfactants cited above, are advantageously selected from the category of surfactants which are allowed by the legislation for pharmaceutical use as a function of the route of administration.

Two surfactants having relatively different properties will advantageously be chosen from the surfactants above, in particular ones having a different hydrophilic lipophilic balance (HLB). The first surfactant will advantageously have a hydrophilic lipophilic balance between 1 and 6, while the second surfactant will have a hydrophilic lipophilic balance between 3 and 15.

As has been seen above, a better control of the size of the multi-layer vesicles can be obtained in proceeding according to French patent FR 2 689 418.

The preparation obtained after the transformation of the liquid crystal lamellar phase into multi-lamellar vesicles may then be diluted, in particular with an aqueous solvent in order to thus obtain an aqueous suspension of vesicles.

As set forth above, one of the drawbacks of the nucleic acid vectors known to date, in particular liposome-type vectors, is to only rarely enable exceeding encapsulation yields of 30%. The method used for the preparation of the vesicles according to the invention enables, itself, reaching yields of encapsulation which can be in the region of 100%. However, such an encapsulation yield, due to the fact of the high activity obtained by virtue of the particular structure of the vesicles of the invention does not always prove necessary.

Thus, the encapsulation yield of the nucleic acid(s) in the compositions of the invention is advantageously at least 10%, preferably at least 40% but can also be between 60 and 100%, and this represents a further advantage with respect to the technologies of the prior art.

The compositions of the invention which contain vesicles which include at least one nucleic acid may be used for in vitro applications, in particular for transforming a cell line, in particular for immortalising or modifying the expression of one or more genes therefrom.

The invention provides a means of vectorization of nucleic acids, it being possible for this vectorization to be carried out in vivo as well as in vitro.

These vesicles can also be used for the preparation of pharmaceutical compositions which can be used in gene therapy.

DNA or a nucleotide sequence of DNA can be cited as examples of a nucleic acid which can be contained in the vesicles of the invention.

The vesicles can also include a particular gene or a sequence of this gene, more particularly a sequence which encodes a given protein.

The compositions of the invention can also include RNA or a nucleotide sequence of RNA in the vesicles.

According to another variant, an oligonucleotide may also be included in the vesicles, it being possible for this oligonucleotide to be of sense and/or anti-sense type.

The vesicles of the invention are advantageously less than 1 $\mu$m in size, preferably between 0.1 and 1 $\mu$m. According to the method of the patent FR-2 689 418 or WO/FR93/19735, it will be possible for this size to be controlled and to be limited by the application of a homogenous shearing of the liquid crystal phase.

According to particularly interesting variants of the invention, it will be possible for various products to be co-encapsulated with the nucleic acid with the view, in particular, to improving the conditions of action of this nucleic acid, or to bring about supplementary functionalities to that of the product encapsulated.

It will be possible for such compositions to be produced by the method described above, in incorporating the product to be co-encapsulated in combination with the nucleic acid in the liquid crystal phase.

Amongst the products that may be advantageously co-encapsulated with the nucleic acids, products of the <<condensation agent>> type will be cited in particular which form a sort of complex with the nucleic acid which stimulates the <<folding>> of the nucleic acid chain, and this enhances its stability in the presence of nucleases.

The histones, which are proteins, and which exist naturally in the nucleus for condensing DNA, will be cited as a preferred example of condensation agents. Histones have the particularity of remaining perfectly bound to the DNA and thus are susceptible of playing an important role in many genomic reactions. Histones known as nucleosonic histones, which are responsible for the folding of DNA into nucleosomes, more specifically, histones H2A, H2B, H3 and H4, and the histone H1 which does not directly participate in the replication of DNA into nucleosomes, but to the stacking to the latter, will be cited amongst the histones which will advantageously be encapsulated in combination with at least one nucleic acid, in particular with DNA. The use of a mixture of histones Hi, H2A, H2B, H3 and H4 (originating from the thymus of the calf) used with a ratio of 1 $\mu$m of total proteins per $\mu$g of DNA has thus enabled condensing 50 $\mu$g of DNA, with a maximum encapsulation yield, into the vesicles of the invention.

According to other variants of the invention, various enzymes, in particular integration enzymes, recombination enzymes or enzymes intended to optimise the replication of the nucleic acid encapsulated, such as the toposomerases or helicases, will advantageously be co-encapsulated into the multi-lamellar vesicle of the invention.

Thus, according to a variant of the invention, integration enzymes may be co-encapsulated in the multi-lamellar vesicle, the function of which enzymes is to enable the gene introduced into the cell to express itself in a host cell, but, above all, to integrate itself with the genome to give daughter cell lines which keep the function brought about the gene introduced. To date, only the use of retroviruses as DNA vector enables a stable and efficient transfer of genes, via the integration of the viral genome into the host cell. However, all the problems linked to the use of retroviruses in the biomedical field may not be brushed aside. Thus, the power of the technology of the invention is to be able to co-encapsulate DNA with proteins, in particular enzymes which enable this integration, which enzymes are designated by <<integration enzymes>>. Thus, DNA and the tools necessary for its incorporation may thus be brought about in a same vector.

It is thus possible to stimulate this genomic integration by the addition of recombination enzymes, specific of the site, which allow introducing, even eliminating, given nucleotide sequences. This form of recombination is called <<site specific recombination>> since the recombination enzyme called integrase recognises nucleotide sequences which can be introduced into a DNA vector which is susceptible to recombination with the DNA from the host cell. This recombination enzyme approaches specific sites, initiates the reaction of cutting, and of soldering of the DNA.

Other enzymatic tools may also be integrated in the vector. The DNA is replicated in eukaryotic organisms as chromatin in which the DNA is combined strongly with the histones, proteins which may also be used according to the present invention for optimising the quantity of DNA encapsulated. If this condensed structure of stacked nucleosomes acts as a barrier which would stop for example the enzymes responsible for replication, the combination of the DNA condensed with the enzymes such as the topoisomerases or the helicases enables solving the eventual problems of winding of the helix or the opening of same.

As has been seen before, one of the advantages of the compositions of the invention is that they provide a nucleic acid vehicle which does not contain any molecule of cationic character.

However, according to a variant of the invention, it is possible to include certain cationic adjuvants, the presence of the multi-lamellar vesicles of the invention enabling masking their toxicity or increasing their activity. It seems that the effect of certain cationic adjuvants is to enable electrostatically fixing the vesicles onto the cell walls, and this explains the increase in the efficiency of the vectors. Furthermore, it appears that the fact of encapsulating a part of the cationic molecules enables lowering their cytotoxicity, the encapsulation decreases the percentage of cationic molecules which are susceptible of entering in contact with the neighbouring cells.

The encapsulation also enables reducing the concentration of cationic molecule used, by virtue of the synergistic effect which increases the efficiency thereof.

Thence, it is possible to co-encapsulate a cationic adjuvant into the vesicles according to the invention in preventing the drawbacks known according to prior art during the use of such products.

It will also be possible for the vesicles comprising the nucleic acid, according to the particularly interesting variants of the invention, to be modified on the surface with the view to be better recognised by the target sought after. According to this variant, molecules, in general proteins, will be attached to the vesicles, and this will enable them to be recognised specifically by certain targets in the organism, and therefore enable them to increase the selectivity of the transfection on the one hand, and on the other hand, the efficiency thereof. Several methods may be used, in particular recourse to monoclonal antibodies. In every case it is necessary to fix the targeting system onto the surface of the vesicle, in order that its recognition efficiency be maximal. This fixation may be carried out by physical methods (adsorption) or even chemical methods. In both cases, the ease of obtaining and manipulating vesicles of the invention are the major advantages for the success of these graftings of functions onto the surface of the vectors. One of the important applications in the biomedical field is the use of vesicles which have on their surface monoclonal antibodies or Fab fragments, which are specific to receptors of the cell surface implied, for example, in the recognition of viral particles (herpes virus . . . ) and which act as transductor of the cell response.

The invention, according to other essential characteristics, relates to pharmaceutical compositions which contain vesicles as defined above which contain various nucleic acids, in suspension in a pharmaceutically acceptable vehicle.

The invention also relates to the methods of therapeutic treatment which use these compositions.

According to the biological or pharmaceutical activity sought after, various types of nucleic acids may be encapsulated.

Thus, it will be possible for the encapsulation of a complete gene to be carried out with the view to providing a pharmaceutical composition intended to provide a deficient gene or an absent gene. As an example, it will be possible for such a use to be made in a treatment of mucoviscidosis.

The encapsulation of nucleic constructions such as oligonucleotides intended to induce an over-expression of or a reduction in the activity of a specific gene will be able to be used in the applications in cancerology or in virology.

These vectors can also be used in models of vaccination from DNA which encodes an antigenic protein.

RNA can also be vectorized since the vectorization of a complementary nucleotide sequence hybridising to transcript inhibits the reading of the mRNA by the ribosomes and prevents the translation thereof into an active protein.

The invention also concerns the use of compositions defined above as an agent intended to transform a cell line.

The invention therefore relates to a method of in vitro transformation of a cell line, which consists in treating said line with a composition as described above.

More specifically, in this case, a gene is brought up to the level of the nucleus of the cell so that it be intranuclear and/or intrachromosomic in order to modify its proper expression of it and/or the expression of other genes which encode one ore more proteins, or to immortalise a line by the incorporation of a viral gene and/or a viral oncogene.

According to a further advantage of the technology of the invention, the invention provides vesicles which enable carrying out a transfection in the presence of serum, and this is impossible to carry out with vesicles of the prior art. This constitutes a considerable progress which enables envisaging for the first time the use of surfactant-based vesicles in vivo.

This point was verified by in vitro transfection tests on cell lines, and on primary cultures of differentiated human cells. It has been possible for results of transfection, which are as good in the presence of foetal calf serum as in the absence of foetal calf serum, to be obtained when other artificial vectors known at the present time (cationic lipids) do not function in such a medium. The latter result is fundamental because it is a sine qua non condition of in vivo use.

The first in vivo transfection results are very encouraging. These results have shown that the transfer of genes could take place in a tumour site and in systemic injection. The intravenous injection, in the animal, of vesicles according to the invention encapsulating the β-galactosidase gene enables inducing a galactosidase activity in various organs (the heart, the lungs and the liver). This point is very encouraging for the use in therapeutic goals of the procedure.

Thus, the invention also relates to the use of multilamellar vesicles of onion structure for the preparation of a pharmaceutical composition intended to correct or to alleviate a deficient or altered cell function or to bring about a new function to a cell, notably in the field of cancerology, of virology or in the correction of bone defects.

Thus, the applications of this vector touch several biomedical research fields, in particular cancerology. In this field, the first results have been obtained in mice bearing tumours. Injections of vesicles which encapsulate a reporter gene have been carried out and a gene activity has been identified at the level of the tumour. It therefore becomes possible to envisage the use of such vectors which bear genes which encode antimitotic factors, or implicated in apoptosis phenomena (cell death) in order to study the effect of this transfer of genes upon the regression of the tumour.

Moreover, another advantage of this vector is to also function in vivo at the level of a given implantation site. Another field of application of these vectors relates to the actual methods of bone substitution. The implantation, in a bone fault, of vesicles which bear the gene which encodes the osteoinducing proteins known by the term <<BMPs>> which corresponds to <<Bone Morphogenetic Proteins >>, would stimulate osteogenesis. If the future of these osteoinducing factors in the orthopaedic field is very promising, at the present time, the major problem of the vectorization, of the regulation of the delivery system at the site of the implantation without observing any systemic effect, does nevertheless remain to be solved. The present invention provides for the first time an acceptable vector. Furthermore, the systemic injections of vesicles bearing the β-galactosidase gene, and the first biodistribution experiments have shown a genic activity in various organs. The use of such a method combined with a targeting, as described above, offers great therapeutic perspectives.

BRIEF DESCRIPTION OF THE DRAWINGS

The examples given below are given with reference to FIGS. 1 to 3 which, respectively, represent.

DESCRIPTION OF THE PREFERRED EMBODIMENTS

The quantities and proportions given in the Examples are by weight unless otherwise indicated.

EXAMPLE 1

Protection against DNAse

The aim of this Example is to demonstrate the efficiency of the multilamellar microvesicles according to the invention for encapsulating a DNA and protecting it from the action of the enzyme DNAse. For this, a grafted DNA (DNA-DIG) is encapsulated according to the method of the invention. The microvesicles which contain the DNA, as well as free DNA, are then submitted to the action of the enzyme. The integrity of the DNA is then revealed by hybridisation of the complementary DNA and coloration. It is thus observed that the DNA encapsulated according to the method is intact, while the free DNA was destroyed by the enzyme.

a) Preparation of the Sample

10 µl of a 1 µg/50 µl solution of DNA-DIG (Boehringer Mannheim), i.e. 200 ng of DNA-DIG are mixed with 375 µl water, 100 mg of ethoxylated lauric alcohol having 4 molecules of ethylene oxide (laureth 4 for example Lauropal-4-Witco) and 525 mg of soya lecithin having 90% of phosphatidylcholine (Phospholipon P90. Natterman). The water is sterilised beforehand by filtering over a 0.25 µm filter, while the surfactants are treated with UV rays. After mixing at ambient temperature, during which care is taken to apply a homogeneous and uniform shearing over all the sample, a paste is obtained which corresponds to the liquid crystal phase and which is arranged in the form of a compact assembly of microvesicles. This paste is left to stand for 24 hours.

For their use, a dispersion of the microvesicles is prepared by diluting 50 mg of paste in 1 ml of sterile water.

b) Characterisation

Figure 1:
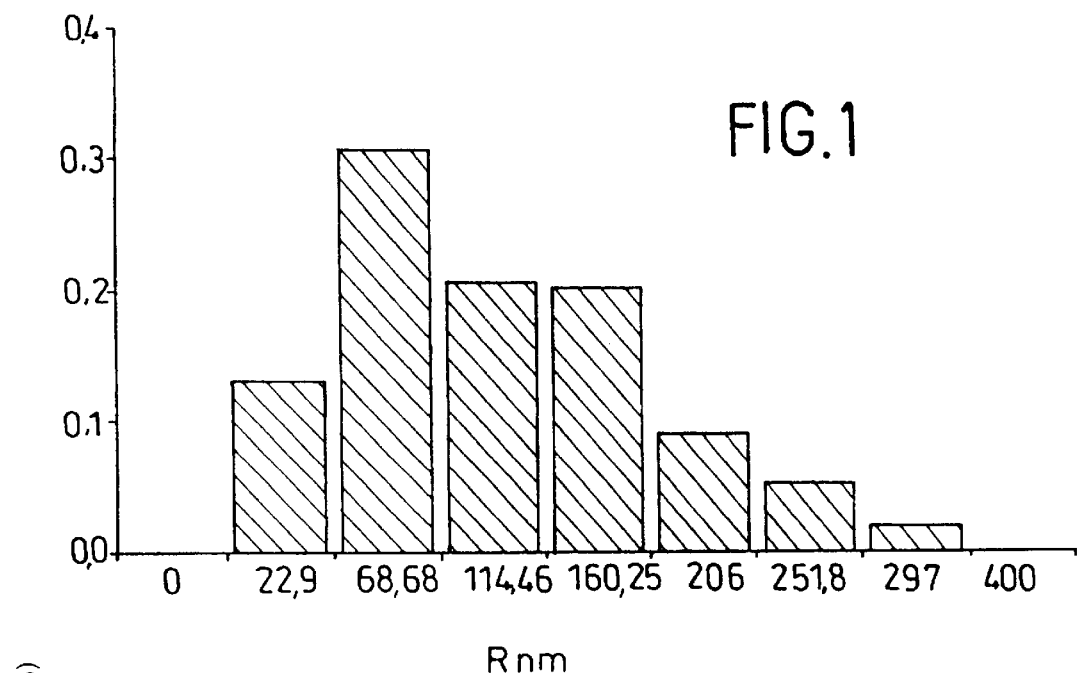
FIG. 1: the histogram of the rays expressed in nm of the multi-lamellar vesicles prepared according to Example 1.

The size of the microvesicles is measured by dynamic light diffusion on a 1% dispersion of the paste in water. A value of the diameter of about 0.2 µm is obtained. This value is confirmed by electronic microscopy (cryofracture). The results of size measurement are indicated in FIG. 1 which gives a histogram of the size distribution observed by microscopy. A more precise inspection of the size can be obtained in using the method described in the patent WO-A-93 19735.

c) Test Method

A basic dispersion of DNA-containing microvesicles is prepared from 50 mg of paste dispersed in 1 ml of water. This basic dispersion is then diluted in water in order to obtain 5 test dispersions, which contain from 10 ng/ml to 1 pg/ml of DNA, by variation of a factor 10. Solutions of free DNA-DIG are prepared of the same concentrations to serve as control solutions.

These dispersions are placed in contact for 1 h at 37° C. with a solution of DNAse I (Boehringer Mannheim) in a proportion of 2 units of DNAse for 1 µg of DNA. In a second step, the presence or not of DNA-DIG is revealed by fixing onto a nitrocellulose membrane (Hybond-C super) and then by hybridisation with the complementary DNA-DIG in using the "dot-blot" technique. The membrane is then revealed by coloration with NBT/BCIP according to the method developed by Boehringer Mannheim and published in Genius, Applications Manuel, Boehringer-Mannheim Biochemicals Indianapolis 5–7, 1989.

d) Results

It is noticed by "dot-blot" analysis that:

the free DNA non-treated by the DNAse is visualised by the "dot-blot" technique, the free DNA treated by the DNAse is totally destroyed for all concentrations, the DNA encapsulated according to the method of the invention, non-treated with DNAse is visualised by the same technique, the DNA encapsulated according to the method of the invention, treated with the DNAse, remains clearly visible and is therefore protected from enzymatic action, and the empty microvesicles (without DNA) do not give a visible reaction in the analysis, and this eliminates any risk of a false positive.

A finer analysis of the compared intensity of the "dot-blot" images enables evaluating that about 80% of the DNA was protected from the enzymatic action. It may be deduced that the 20% destroyed correspond to the residual DNA non-encapsulated, and this enables evaluating the level of encapsulation to about 80%. These results were confirmed by an electrophoresis experiment on an agarose gel, which showed no degradation of the DNA.

EXAMPLE 2

Interaction between the encapsulated DNA and cells in culture

The aim of this example is to demonstrate that a DNA encapsulated according to the method of the invention is capable of penetrating inside cells, of being released therefrom, and of reaching the nucleus. For this, a plasmid DNA is coupled to a fluorescent probe, which will allow a visualisation of the cellular incorporation by fluorescence microscopy.

a) Preparation of the Sample

Plasmid DNA (pBR 322, 4363 base pairs, Promega) at a concentration of 0.1 µg/ml is coupled to fluoresceine (YoYo-1 probe, Molecular Probe Inc.) and then encapsulated in multilamellar microvesicles according to the same method as for Example 1, with:

aqueous solution of DNA YoYo: 37.5%

Ethoxylated lauric alcohol ethoxylated having 4 moles of EO: 10%

Soya lecithin (90% of phosphatidylcholine): 52.5% b) Incubation of the Cells

The various cell lines, human fibroblasts (primary culture), NIH 3T3 (ATCC) are kept under classical culture conditions (IMDM, Gibco, Life technology), containing 10% of calf serum (Gibco, Life technology), 10,000 U of penicillin-streptomycin (Gibco, Life technology) at 37° C., in an atmosphere of 5% $CO_2$. The cells are placed in the presence of a 10% dispersion of DNA-containing microvesicles for 5 minutes, in an IMDM medium alone. After this incubation time, the cells are washed to remove the vesicle dispersions and are then visualised.

c) Result

The cells are visualised by fluorescence microscopy, after various duration times of incubation.

At t=O, (for control, before washing) the microvesicles are observed in the supernatant medium as fluorescent dots.

At t=5 min, the fluorescent microvesicles are visualised at the contact of the surface of the cells. The start of an intracytoplasmic diffusion of the fluorescence is noted.

At t=1 hour, the intracytoplasmic diffusion of the fluorescence is observed. The nuclear circumference is clearly apparent, a start of fluorescence at the nucleus appears.

Between t=2 and 8 hours, the fluorescence begins to appear in the nucleus. It remains strong in the cytoplasm.

At t=48 hours, the fluorescence is weaker and only subsists in the proximity of the nuclei.

This example demonstrates that it was possible for the DNA to be incorporated in the fibroblasts, and then has crossed the cytoplasm to reach the nucleus.

EXAMPLE 3

Encapsulation of a gene and demonstration of the transfer And the transient expression of this gene The aim of this example is to demonstrate that a gene encapsulated in the multi-lamellar microvesicles of the invention can be incorporated in the nucleus of a cell and express itself. The test retained is the use of the gene which encodes β-galactosidase, and the expression of which is evidenced by the blue coloration of the nuclei of the transfected cells, during the reaction with the X-GAL substrate. In this example, the efficiency of transfection is compared to that of a commercial vector, LipofectAce® (Life Technology).

a) Preparation of the Microvesicles

The microvesicles containing t he gene which encodes β-galactosidase (LacZ) are prepared according to the method of Example 1, in using an aqueous solution of the gene, at 10 mg/ml. Three types of gene of the modified LacZ type were tested: pRSCLacZ, pCHLacZ and pRSVLacZ-Sal-1. Each gene was co-encapsulated with polylysine at a concentration of 100 µM, of molecular weight of either 3.5 kDa, or 10 kDa. The comparison of the microvesicles is the following Soya lecithin having 90% phosphatidylcholine . . . 41.5%

Cholesterol (Sigma) . . . 3.5%

Potassium oleate . . . 5%

Aqueous solution of DNA and polylysine . . . 49.5%

For the incubation of the cells, the microvesicles are dispersed in water, so as to obtain an incubation medium containing 10 µg/ml of DNA.

b) Transfection

The cells (human fibroblasts, primary culture) are kept under classical culture conditions as in Example 2. For the incubation, the medium is replaced by an IMDM medium containing 100 µM of chloroquine, and without serum. The incubation with the microvesicles lasts from 2 to 12 hours. The cells are then washed and kept in culture for 48 hours in a complete medium (IMDM, serum, penicillin-streptomycin).

The visualisation of the transfection is carried out by washing the cells, fixing, and adding the substrate X-GAL (Biosynth AG). This substrate is cleaved by the enzyme corresponding to the β-galactosidase gene, in giving a deep blue precipitate which is exclusively intracellular due to the intranuclear signal generally designated by <<nis>>, according to the terminology "nuclear localisation signal".

The same experiment is carried out for comparison, in using a commercial vector LipofectAce® (Life Technology), used according to the method of the manufacturer, with the same concentrations of the gene.

c) Result

Figure 2:
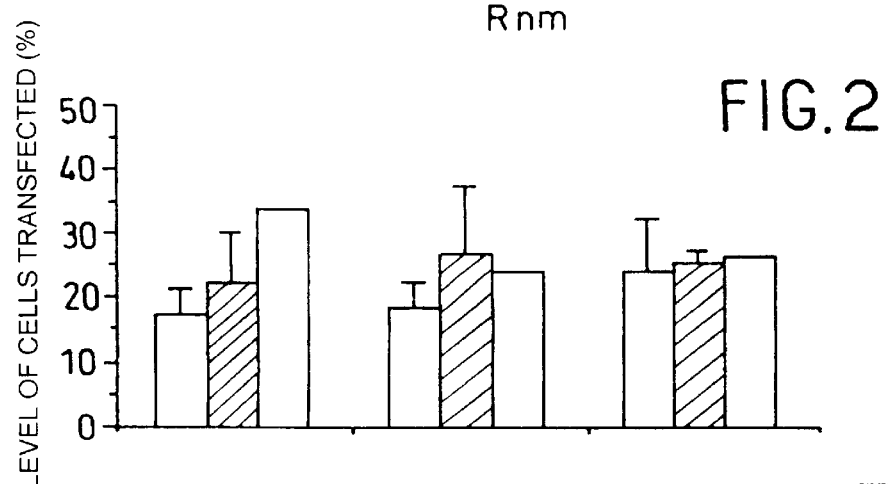
FIG. 2, given with reference to Example 3, the efficiency of the transfection of the β-galactosidase gene on the fibroblastic cells of human skin for two types of different formulations according to the invention and one commercial vector.

The results, which are in the form of percentage cells transfected are given in FIG. 2. Each histogram corresponds to one of the genes (from left to right: pRSCLacZ, pCHLacZ and pRSVLacZ-Sal-1). On each one, the percentage transfection obtained is given with, from left to right LipofectAce®, the micro-vesicles with 3.5 kDa polylysine and the microvesicles with 10 kDa polylysine.

It is noted that, in every case, the results are better by using the microvesicles than with the commercial vector. Percentages from 25 to 35% of transfection are obtained in the case of the microvesicles.

A DNAse test, identical to that described in Example 1, may be carried out on this reporter gene, by using a $^{32}$P-labelled cDNA for the <<dot-blot>> technique. It is then noted, as in Example 1, that the DNA encapsulated in the microvesicles according to the invention is not destroyed by the DNAse. On the contrary, the observed encapsulation yield is lower. The same test of protection against DNAse is carried out on the same gene, vectorised by the commercial product, shows no protection of this type of vector, and this might explain the low level of transfection obtained for this commercial product.

EXAMPLE 4

Encapsulation of a gene and demonstration of the transfer and the transient expression of this gene: effect of cationic adjuvants The aim of this example is to demonstrate the possibility of the use of adjuvants of the cationic type for improving the efficiency of the transfection. The adjuvant used is a polymer, polyethyleneimine. Several tests are carried out, under conditions analogous to those of Example 3 (transfection of the β-galactosidase gene), but without using polylysine. For comparison, two formulations with polylysine, but without adjuvant, are prepared, one identical to that of Example 3 (lecithin, potassium oleate, cholesterol), the other identical to that of Example 1 (lecithin, laureth 4). Finally, for a control, three transfection experiments are carried out by using either a commercial vector LipofectAce® (Life Technology), or non-encapsulated DNA complexed to polyethyleneimine.

a) Preparation of the Microvesicles

The method is strictly identical to that used in Example 3, by using pRSVLacZ as gene. Polyethyleneimine (molar mass 50 kDa, Sigma) is added to the aqueous solution of DNA before encapsulation at two concentrations: 10 mM and 100 μM.

The controls without polyethyleneimine are prepared according to the method of Example 3 (lecithin, cholesterol, potassium oleate), or of Example 1 (lecithin, laureth 4).

b) Transfection

The method is identical to that of Example 3. The transfection is carried out on human fibroblasts (primary culture). In every case, the gene concentration in the incubation medium is 10 μg/ml.

The experiments with non-encapsulated DNA are carried out by introducing into the incubation medium, instead of the dispersion of vesicles according to the invention, a pre-mixed solution containing DNA and polyethyleneimine.

c) Result

Figure 3:
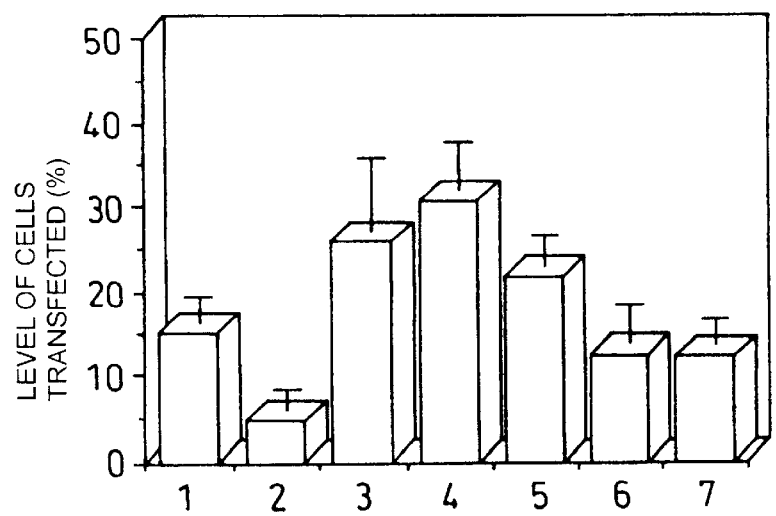
FIG. 3, given with reference to Example 4, the comparative results of the efficiency of the transfection of the, β-galactosidase gene on human fibroblasts in using various formulations of microvesicles according to the invention, which contain or do not contain a cationic adjuvant, in comparison with a commercial vector.

The results, which are given in the form of a histogram of the percentage of transfected cells, are given in FIG. 3. The results correspond, from left to right, to the following tests:

1—microvesicles based on lecithin and potassium oleate

2—microvesicles based on lecithin and lauric alcohol having 4 molecules of ethylene oxide (laureth 4)

3—microvesicles based on lecithin and potassium oleate, co-encapsulating polyethyleneimine, at a concentration of 10 mM 4—microvesicles based on lecithin and potassium oleate, co-encapsulating polyethyleneimine, at a concentration of 100 μM 5—DNA complexed to polyethyleneimine, with a polymer concentration of 10 mM 6—DNA complexed to polyethyleneimine, with a polymer concentration of 100 μM 7—Use of the commercial vector LipofectAce® (Life Technology).

It is observed that by virtue of the co-encapsulation of the polyethyleneimine, the level of cells transfected reaches 35%. The DNA which is non-encapsulated, but simply complexed by the polyethyleneimine, is also transfected but has then a level of transfection which is not as good. All the tests carried out with vectors based on potassium oleate, with or without adjuvant, give a result better than the commercial vector.

EXAMPLE 5

Encapsulation of a gene and demonstration of the transfer and the transient expression of this gene: effects of non-cationic adjuvants The aim of this example is to demonstrate the possibility of co-encapsulating non-cationic adjuvants of condensation of DNA in order to improve the efficiency of transfection. The adjuvant used is a mixture of histones H1, H2a, H2b, H3, H4 from the thymus of a calf (supplier: Boehringer). The DNA used is the same as that used in Example 4.

a) Condensation of the DNA by histones

The DNA is condensed beforehand by simultaneously placing in solution an equal weight of DNA and of the mixture of histones H1, H2a, H2b, H3, H4 from the thymus of a calf (50 μg of DNA with 50 μg of histones mixture in 12 μl of water) and incubating the mixture for 10 min at 37° C.

b) Preparation of the microvesicles

The method is strictly identical to that used in Example 3, by using the solution of the DNA/histones mixture instead of the gene solution.

The composition by weight of the vesicles is:

| | |
|---|---|
| soya lecithin having 90% of phosphatidyl choline: | 31.5% |
| cholesterol | 6.5% |
| lauric alcohol ethoxylated having 4 EO | 2% |
| aqueous solution of the DNA/histones mixture | 60% | c) Measurement of the encapsulation yield

1 μg of DNA was labelled with $^{32}$P (according to the method known as random priming) and mixed with 49 μg of non-labelled DNA (to respect the amount of 50 μg of DNA). This DNA is encapsulated and then the vesicles are dispersed in water. The suspension is ultra-centrifuged at 30,000 rpm for 45 minutes. The supernatant is separated off from the plug and each one is counted in a β-counter in order to evaluate the radioactivity present.

The yield of encapsulation measured is always greater than 80%.

d) Transfection

Transfection tests are carried out on human skin fibroblasts according to an incubation and counting method which is identical to that described in Examples 3. The concentration of DNA used in the dispersion placed in contact with the cells is 5 μg/ml.

The percentage transfection under these conditions varies from 20 to 30% (defined as the number of transfected cells with respect to the cells incubated).

What is claimed is:

1. A composition containing a plurality of multilamellar vesicles and at least one nucleic acid, at least one part of which is found included inside said multilamellar vesicles, wherein said vesicles are obtained by rearrangement of a lamellar liquid crystal phase comprising at least one surfactant and incorporating at least one nucleic acid by shearing or mechanical stirring, and wherein each said vesicle comprises a succession of lamellar bi-layers extending from each vesicle center to its outermost layer and comprising at least one surfactant agent, said bi-layers being concentric and separated by a liquid medium.

2. The composition according to claim 1, wherein the size of said vesicles is less than 1 µm.

3. The composition according to claim 1, wherein the surfactant agent is a non-cationic surfactant.

4. The composition according to claim 3, wherein said non-cationic surfactant is selected from the group consisting of:

hydrogenated or non-hydrogenated phospholipids, saturated or mono- or polyunsaturated, linear or branched $C_6$ to $C_{18}$ fatty acids, in the form of an acid or an alkali metal salt, an alkaline earth metal salt, or an amine salt, ethoxylated or non-ethoxylated esters of the saturated or mono- or polyunsaturated, linear or branched $C_6$ to $C_{18}$ fatty acids and a member selected form the group consisting of sucrose, sorbitan, mannitol, glycerol, polyglycerol and glycol, mono-, di- or triglycerides or mixtures of glycerides of the saturated or mono- or polyunsaturated, linear or branched $C_6$ to $C_{18}$ fatty acids, saturated or mono- or polyunsaturated, linear or branched, ethoxylated or nonethoxylated $C_6$ to $C_{18}$ fatty alcohols, ethoxylated or non-ethoxylated ethers of the saturated or mono- or polyunsaturated, linear or branched, ethoxylated or nonethoxylated $C_6$ to $C_{18}$ fatty alcohols and a member selected form the group consisting of sucrose, sorbitan, mannitol, glycerol, polyglycerol and glycol, hydrogenated or non hydrogenated polyethoxylated vegetable oils, block polymers of polyoxyethylene and polyoxypropylene (poloxamers), polyethylene glycol hydroxystearate, and sterol-skeleton alcohols.

5. The composition according to claim 1, wherein the bi-layers of said vesicles comprise at least two surfactant agents, one of which has a hydrophilic lipophilic balance (HLB) between 1 and 6 and the other has a hydrophilic lipophilic balance (HLB) between 3 and 15.

6. The composition according to claim 1, wherein at least 10% of said at least one nucleic acid is found included inside said multilamellar vesicles.

7. The composition according to claim 6, wherein 60 to 100% of said at least one nucleic is found included in said vesicles.

8. The composition according to claim 1, wherein said nucleic acid is DNA or a nucleotide sequence of DNA.

9. The composition according to claim 1, wherein said nucleic acid is a gene or sequence of a-gene encoding a protein.

10. The composition according to claim 1, wherein said nucleic acid is RNA or a nucleotide sequence of RNA.

11. The composition according to claim 1, wherein said nucleic acid is a sense and/or antisense oligonucleotide.

12. The composition according to claim 1, wherein said vesicles further contain a cationic adjuvant co-encapsulated with said nucleic acid.

13. The composition according to claim 1, containing at least one co-encapsulated product selected from the group of DNA condensing agents, integration or recombination enzymes, and enzymes intended to optimize the replication of the encapsulated nucleic acid.

14. The composition according to claim 1, wherein said vesicles are surface modified addition of molecules enabling recognition by a target in an organism to be treated therewith.

15. A method of preparation of a composition according to claims 1, comprising the steps of preparing a lamellar liquid crystal phase incorporating said nucleic acid and rearranging said liquid crystal phase into multilamellar vesicles by the application of a shearing.

16. A composition containing vesicles as defined in claim 1, in suspension in a pharmaceutically acceptable vehicle.

17. The composition according to claim 16, wherein said encapsulated nucleic acid is a complete gene.

18. The composition according to claim 16, wherein said nucleic acid is an oligonucleotide intended to induce an over-expression of or a reduction in the activity of a specific gene.

19. The composition according to claim 16, which is a vaccine, said nucleic acid being a DNA encoding an antigenic protein.

20. A method of in vitro transformation of a cell line or of a primary cell culture of differentiated human cells, comprising treating said line or primary culture with a composition according to claim 8, resulting in uptake and expression of the DNA.

21. In a method for delivery of a nucleic acid to a cell to alter a cell function or to cause a new cell function, the improvement comprising delivery to the cell of a composition containing a plurality of multilamellar vesicles and at least one said nucleic acid, at least part of which is found included inside said multilamellar vesicles, wherein each said vesicle comprises a succession of lamellar bi-layers extending from each vesicle center to its periphery and comprising at least one surfactant agent, said bi-layers being concentric and separated by a liquid medium.

22. The composition according to claim 2, wherein the size of said vesicles is between 0.1 and 1 µm.

23. The composition according to claim 6, wherein at least 40% of said at least one nucleic acid is found included inside the vesicles.

24. The composition according to claim 9, wherein said nucleic acid is a sequence encoding a protein.

* * * * *

UNITED STATES PATENT AND TRADEMARK OFFICE
CERTIFICATE OF CORRECTION

PATENT NO. : 6,387,396 B2
DATED : May 14, 2002
INVENTOR(S) : Patrick Mahy et al.

It is certified that error appears in the above-identified patent and that said Letters Patent is hereby corrected as shown below:

<u>Title page,</u>
Item [57], ABSTRACT,
Line 1, change "multicellular" to -- multilamellar --.

Signed and Sealed this

Thirty-first Day of December, 2002

JAMES E. ROGAN
*Director of the United States Patent and Trademark Office*